United States Patent [19]
Nastasi et al.

[11] Patent Number: 5,817,326
[45] Date of Patent: Oct. 6, 1998

[54] PROCESSING OF HYDROXYLAPATITE COATINGS ON TITANIUM ALLOY BONE PROSTHESES

[75] Inventors: Michael A. Nastasi, Espanola, N. Mex.; Timothy E. Levine, Santa Clara, Calif.; James W. Mayer; Vincent B. Pizziconi, both of Phoenix, Ariz.

[73] Assignee: The Regents of the University of California, Los Alamos, N. Mex.

[21] Appl. No.: 566,339

[22] Filed: Dec. 1, 1995

[51] Int. Cl.⁶ ........................................................ A61F 2/28
[52] U.S. Cl. ............................... 424/426; 523/115; 623/16
[58] Field of Search ..................................... 424/423, 426; 523/115; 623/16

[56] References Cited

U.S. PATENT DOCUMENTS

| | | |
|---|---|---|
| 4,908,030 | 3/1990 | Linkow et al. . |
| 5,205,921 | 4/1993 | Shirkanzadeh ........................... 205/318 |
| 5,279,831 | 1/1994 | Constantz et al. . |

OTHER PUBLICATIONS

Y. Ohtsuka et al., Surf. Coat. Tech. 65, 224 (1994).
Timothy E. Levine et al., "Ion–Beam–Induced Densification of Sol–Gel Ceramic Thin Films," J. Vac. Sci. Technol. B 12, 986 (1994) (Levine 1).
Timothy E. Levine et al., "Ion–Beam–Induced Densification Of Zirconia Sol–Gel Thin Films," J. Am. Ceram. Soc. 76, 1369 (1993) (Levine 2).
T. Brendel et al., "A Polymeric Route For The Synthesis Of Hydroxyapatite Coatings," J. Mat. Sci., Materials in Medicine 3, 175 (1992).
Q. Qiu et al., "Bone Growth Of Sol–Gel Calcium Phosphate Thin Films In Vitro," Cells and Materials 3, 351 (1993).
R. Pascual et al., "Rapid Thermal Processing Of Zirconia Thin Films Produced By The Sol–Gel Method," J. Appl. Phys. 70, 2348 (1991).
F. Erdogan, "Fracture Mechanics Of Functionally Graded Materials," MRS Bulletin, p. 43 (Jan. 1995).
Timothy E. Levine et al., "Ion Beam Mixing Of Titanium Overlayers With Hydroxylapatite Substrates," Mat. Res. Soc. Symp. Proc. 356, 791 (1995) (Levine 3).
R. A. McGill et al., J. Vac. Sci. Technol. A11, 2856 (1993).
T. L. Alford et al., "Ion Mixing Of Pulsed Laser Deposited Hydroxylapatite (HA)," Mat. Res. Soc. Symp. Proc. 354, 15 (1995).

*Primary Examiner*—Carlos A. Azpuru
*Attorney, Agent, or Firm*—Samuel M. Freund

[57] ABSTRACT

Processing of hydroxylapatite sol-gel films on titanium alloy bone prostheses. A method utilizing non-line-of-sight ion beam implantation and/or rapid thermal processing to provide improved bonding of layers of hydroxylapatite to titanium alloy substrates while encouraging bone ingrowth into the hydroxylapatite layers located away from the substrate, is described for the fabrication of prostheses. The first layer of hydroxylapatite is mixed into the substrate by the ions or rapidly thermally annealed, while subsequent layers are heat treated or densified using ion implantation to form layers of decreasing density and larger crystallization, with the outermost layers being suitable for bone ingrowth.

8 Claims, No Drawings

PROCESSING OF HYDROXYLAPATITE COATINGS ON TITANIUM ALLOY BONE PROSTHESES

FIELD OF THE INVENTION

The present invention relates generally to hydroxylapatite-coated titanium alloy bone implants and, more particularly, to improving the adhesion of hydroxylapatite coatings to titanium alloy substrates for use in bone implantation. The invention was made with government support under Contract No. W-7405-ENG-36 awarded by the U.S. Department of Energy to the Regents of The University of California. The government has certain rights in the invention.

BACKGROUND OF THE INVENTION

The challenge in any prosthesis implantation is affixing the prosthesis to the underlying bone. For elderly patients, doctors simply use bone cement to glue a stainless steel alloy prosthesis to the bone. This procedure is inexpensive and usually survives the lifetime of the patient. For younger patients who are more physically active, however, physicians use titanium alloy implants because of the metal's light weight, corrosion resistance and flexibility. In place of cement, bone growth is encouraged around the metal implant in order to strengthen the bone/implant assembly. Typically, by coating the implant with a thin layer of hydroxylapatite, a calcium-phosphate-bioceramic material ($Ca_{10}(PO_4)_6(OH)_2$) which has been found to be biocompatible, and which comprises about 75% of bone matter, bone may be induced to grow onto the implant.

Current hydroxylapatite (HA) coating technology includes radiofrequency (RF) sputtering and plasma spray. Radiofrequency sputtering can produce very thin coatings (~20 $\mu$m) having improved adhesion, but the coatings are amorphous and phosphorous deficient. Plasma spray is presently the only practical commercial method that produces relatively thick (50–200 $\mu$m) porous HA coatings on irregular-shaped prostheses.

Although porous HA coatings hold promise in overcoming aseptic loosening of implant devices, plasma sprayed HA films have been shown to have poor mechanical adhesion resulting in premature separation and subsequent implant failure. In addition, plasma spraying, without more, lacks control of HA microstructure which results in suboptimal tissue responses.

Ion implantation has provided reproducibility, control and short processing times for materials modification to the field of microelectronics for approximately twenty years. More recently, ion beams have been used to modify the structure and properties of ceramic materials. Although dynamic ion mixing of HA with titanium substrates has been observed when porous and amorphous HA films were irradiated during deposition (See, e.g., Y. Ohtsuka et al., Surf. Coat. Tech. 65, 224 (1994)), until the present invention there has been no observation of ion mixing effects using chemically inert gas species implanted into a fully dense, polycrystalline substrate in a process that is suitable for industrial production of devices. Ion mixing effects are to be distinguished from ion beam sputtering coating techniques as described in U.S. Pat. No. 4,908,030 for "Method Of Manufacturing Synthetic Bone Coated Surgical Implants," which issued to Leonard I. Linkow et al. on Mar. 13, 1990.

Ion beams have also been found to produce densification of sol-gel ceramic thin films (See, e.g., "Ion-Beam-induced Densification Of Sol-Gel Ceramic Thin Films," by Timothy E. Levine et al., J. Vac. Sci. Technol. B 12, 986 (1994) (Levine 1), and "Ion-Beam-Induced Densification Of Zirconia Sol-Gel Thin Films," by Timothy E. Levine et al., J. Am. Ceram. Soc. 76, 1369 (1993) (Levine 2)). Calcium phosphate compounds such as HA have recently been synthesized in the form of bulk powders or as coatings by sol-gel processes (See, e.g., "A Polymeric Route For The Synthesis Of Hydroxyapatite Coatings," by T. Brendel et al., J. Mat. Sci., Materials in Medicine 3, 175 (1992), and "Bone Growth Of Sol-Gel Calcium Phosphate Thin Films In Vitro," by Q. Qiu et al., Cells and Materials 3, 351 (1993)). Densification of sol-gel films may also be achieved by rapid thermal processing (See, e.g., "Rapid Thermal Processing Of Zirconia Thin Films Produced By The Sol-Gel Method," by R. Pascual et al., J. Appl. Phys. 70, 2348 (1991)). However, although this procedure avoids substrate damage for materials which cannot be exposed to high temperatures for long periods, rapid thermal processing is not the method of choice for thermally sensitive substrates.

It is known that in thin films, coatings and layered materials, surface cracking and debonding or delamination are a common form of mechanical failure, and that one effective manner of reducing residual and thermal stresses and enhancing bonding strength has been to eliminate material-property discontinuities by grading the material composition near the interfaces or through the coating. Such materials are known as functionally graded materials (See, e.g., "Fracture Mechanics Of Functionally Graded Materials," by F. Erdogan, MRS Bulletin, p. 43 (January 1995)). The application of several layers of hydroxylapatite onto prosthetic implants is described in U.S. Pat. No. 5,279,831 for "Hydroxyapatite Prosthesis Coatings," which issued to Brent R. Constantz et al. on Jan. 18, 1994. Therein, a first layer having small crystals achieved by establishing conditions which result in a high density of heterogeneous nucleation sites so that there are a large number of hydroxylapatite nucleation sites on the substrate, is followed by at least one additional layer deposited under conditions which provide for a lower level of nucleation so as to produce substantially larger crystals from those closer to the substrate. Such larger crystals are suspected of inducing bone ingrowth and strong bonding between natural bone and the coating. However, no mention is made of further processing the layers after deposition thereof, and the hydroxylapatite is deposited from a reaction mixture of calcium and phosphate sources. Hydroxylapatite sol-gel technology is not employed.

Accordingly, it is an object of the present invention to provide a process for producing coated metallic prosthetic devices which bond strongly to the bone material that surrounds the bone intended to be replaced by the device by encouraging bone ingrowth into the coating, while retaining immunity from delamination and separation of the coating from the metal.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for strengthening the adhesion of hydroxylapatite coatings to titanium alloy prostheses hereof includes the steps of: preparing a sol-gel of hydroxylapatite; coating the titanium alloy prosthesis with a layer of the sol-gel having a chosen thickness; causing the sol-gel layer to densify; and intermixing the titanium alloy with hydroxylapatite and further densifying the already hardened hydroxylapatite layer using non-line-of-sight ion implantation, wherein the thickness of the hydroxylapatite layer is chosen such that ions from the ion implantation step can penetrate the densified hydroxylapatite layer and travel into the titanium alloy prosthesis.

Preferably, the present method further comprises the steps of: coating the ion-beam-implanted titanium alloy prosthesis with a second and subsequent layers of hydroxylapatite sol-gel; curing the prosthesis coated thereby after each layer is applied to drive off water; and heating the coated and cured prosthesis to densify the second and subsequent layers of hydroxylapatite before the next layer is applied, wherein the final layer has suitable density and crystal properties for encouraging bone ingrowth.

In a further aspect of the present invention and in accordance with its objects and purposes, the method for strengthening the adhesion of hydroxylapatite coatings to titanium alloy prostheses may also include the steps of: preparing a first sol-gel of hydroxylapatite having a chosen density; coating the titanium alloy prosthesis with the sol-gel; curing the coated prosthesis to form a first layer of hydroxylapatite; densifying the first layer of hydroxylapatite such that the first layer has acceptable binding characteristics to the prosthesis; preparing a second sol-gel of hydroxylapatite having a lower density than the first sol-gel thereof; coating the densified hydroxylapatite layer with the second layer of hydroxylapatite sol-gel; curing the coated prosthesis to form a second layer of hydroxylapatite; and densifying the second layer of hydroxylapatite such that the second layer is suitable for bone ingrowth.

It is preferred that the step of densifying a layer of hydroxylapatite is accomplished using rapid thermal annealing.

Preferably also, the step of densifying a layer of hydroxylapatite is accomplished using non-line-of-sight ion implantation.

Benefits and advantages of the present invention include improved bonding between the hydroxylapatite and the titanium alloy substrate without having to significantly heat the prosthesis, and good control over the crystalline/amorphous phase ratio, porosity and film thickness of additional layers of hydroxylapatite such that the ingrowth of bone can be encouraged.

DETAILED DESCRIPTION

Briefly, the present invention includes a method utilizing non-line-of-sight ion implantation and/or rapid thermal processing to provide improved bonding of layers of hydroxylapatite to titanium alloy substrates (such as Ti-6Al-4V), while encouraging bone ingrowth into the hydroxylapatite layers located away from the substrate, for the fabrication of prostheses. The first layer of hydroxylapatite is mixed with the substrate by the ions or rapidly thermally annealed, while subsequent layers are heat treated to form layers of decreasing density and larger crystallization, with the outermost layers being suitable for bone ingrowth.

In order to demonstrate the mixing of titanium and hydroxylapatite using ion mixing, articles having titanium deposited onto solid hydroxylapatite were investigated. A pellet of HA was formed from commercially available pure HA powder which was pressed at 8.5 Mpa and heat treated at a heating and cooling rate of 200° C./hr in a 3-zone furnace according to the following steps. The pellet was first heated to 800° C. for 1 hour and then cooled to room temperature. Upon reaching room temperature, the pellet was then heated to 1400° C. for 12 hours and cooled to room temperature. A flat surface was polished on the pellet, 1 cm in diameter with an average roughness of about 20 nm. A titanium film of approximately 140 nm thickness was deposited on the sample using electron beam deposition. Half of the sample was masked using aluminum foil. The half-masked sample was subsequently implanted using a 290 keV Ar ion beam to a dose of $5\times10^{16}$ Ar/cm$^2$ at a dose rate of $5\times10^{12}$ Ar/cm$^2$/s at room temperature. The implanter had a base pressure of $3\times10^{-4}$ Pa. In performing analysis of the implanted sample by observing the secondary ion mass spectroscopy (SIMS) depth profile signals for titanium and calcium, it was assumed that the sputter rates of the as-deposited and implanted sides of the sample are identical. Additionally, while ion mixing phenomena are attendant to SIMS depth profile studies, the energy of the sputtering ion beam was approximately one-tenth of that for the implanted ions at the interface. Therefore, comparison of Secondary Ion Mass Spectrometer (SIMS) depth profiles between the as-deposited and implanted samples are a useful measure of mixing from implantation. It was observed that the titanium/HA interface was broadened as a result of ion beam mixing. Actual SIMS depth profile traces of titanium and calcium signals of as-deposited and implanted sample may be found in "Ion Beam Mixing Of Titanium Overlayers With Hydroxylapatite Substrates," by Timothy E. Levine et al., Mat. Res. Soc. Symp. Proc. 356, 791 (1995) (Levine 3). Adhesion was tested using techniques described by R. A. McGill et al., in J. Vac. Sci. Technol. A11, 2856 (1993). The force required to separate the titanium film from the HA substrate was found to increase upon ion irradiation. At a force where the as-deposited film completely failed, partial adherence was observed in the implanted film. Moreover, the high degree of contrast exhibited in the wear track of the unimplanted film is indicative of substrate exposure; the lesser degree of contrast in the wear track of the implanted film indicates that the substrate has not been exposed. It is therefore concluded that these effects are a result of the mixing of the film with the substrate.

Although a similar experiment has not been performed by the present inventors for HA deposited and processed by sol-gel methods and plasma source ion implantation onto titanium-based alloys, in "Ion Mixing Of Pulsed Laser Deposited Hydroxylapatite (HA)," by T. L. Alford et al., Mat. Res. Soc. Symp. Proc. 354, 15 (1995), ion mixing under conditions similar to those of Levine 3, supra, has been shown to induce mixing in HA/Ti films where a thin layer of HA was deposited on titanium substrates using pulsed laser deposition.

In a practical application, HA would be deposited onto the prosthesis using an industrially proven technique such as plasma spraying of a sol-gel thereof. This permits nonplanar structures to be coated. Levine 1 and Levine 2, and Levine 3, supra, teach that densification and mixing may be achieved by ion beam implantation, respectively, and Pascual, supra, teaches that rapid thermal processing of thin films produces densification. Since U.S. Pat. No. 5,279,831, supra, teaches that a high density of heterogeneous nucleation sites produces strongly adherent HA coatings, it is clear that either ion beam implantation or densification will result in a strongly adherent HA coating. The thickness of the coating is limited by the requirement that ions may pass therethrough into the substrate. Adjusting the viscosity and the density of the sol-gel will permit a chosen hydroxylapatite thickness to be achieved.

Subsequent layers are added to provide a gentle density gradient in accordance with Erdogan, supra, with the outermost (lower density) layers permitting bone ingrowth; the final layered prosthesis providing greater strength than those presently available. It is anticipated that the total coating thickness would optimally be between 50 and 200 $\mu$m. Individual layer thicknesses would be determined principally by the viscosity of the sol-gel which would decrease as the density thereof decreases for the outer layers. Each layer would be cured to drive off water and processed by rapid thermal annealing or ion beam densification in order to avoid thermal damage to the titanium alloy, before the next layer was added. It should be mentioned that even a two layer prosthesis prepared according to the teachings of the present invention would provide increased strength over existing prostheses.

The foregoing description of the invention has been presented for purposes of illustration and description and is not intended to be exhaustive or to limit the invention to the precise form disclosed, and obviously many modifications and variations are possible in light of the above teaching. For example, other ions might be utilized in the ion implantation mixing process, and substrates other than titanium alloys could be employed. Clearly, other methods for HA deposition might be employed. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for strengthening the adhesion of hydroxylapatite coatings to titanium alloy prostheses, which comprises the steps of:
    a. preparing a sol-gel of hydroxylapatite;
    b. coating the titanium alloy prosthesis with a layer of the sol-gel having a chosen thickness;
    c. causing the sol-gel layer to densify; and
    d. intermixing the titanium alloy with hydroxylapatite and further densifying the hardened hydroxylapatite layer using non-line-of-sight ion-implantation; wherein the thickness of the sol-gel layer is chosen such that ions from said ion implantation step can penetrate the densified hydroxylapatite layer and travel into the titanium alloy prosthesis.

2. The method as described in claim 1, further comprising the steps of:
    a. coating the ion-implanted titanium alloy prosthesis with a second layer of hydroxylapatite sol-gel;
    b. curing the prosthesis coated thereby to drive off water; and
    c. heating the coated and cured prosthesis to densify the second layer of hydroxylapatite, wherein the second layer has a density and crystallization suitable for ingrowth of bone.

3. The method as described in claim 1, further comprising the step of coating the ion-beam-implanted titanium alloy prosthesis with a second layer of hydroxylapatite, wherein the second layer has a density and crystallization suitable for ingrowth of bone.

4. The method as described in claim 1, wherein said step of causing the sol-gel layer to harden and density is accomplished using rapid thermal annealing.

5. The method as described in claim 2, wherein said step of heating the coated and cured prosthesis is accomplished using rapid thermal annealing.

6. A method for strengthening the adhesion of hydroxylapatite coatings to titanium alloy prostheses, which comprises the steps of:
    a. preparing a first sol-gel of hydroxylapatite having a chosen density;
    b. coating the titanium alloy prosthesis with the sol-gel;
    c. curing the coated prosthesis to form a first hard layer of hydroxylapatite;
    d. densifying the first layer of hydroxylapatite such that the first layer of hydroxylapatite has acceptable binding characteristics to the prosthesis;
    e. preparing a second sol-gel of hydroxylapatite having a lower density than the first sol-gel thereof;
    f. coating the densified hydroxylapatite layer with the second layer of hydroxylapatite sol-gel;
    g. curing the coated prosthesis to form a second hard layer of hydroxylapatite; and
    h. densifying the second layer of hydroxylapatite such that the second layer is suitable for bone ingrowth.

7. The method as described in claim 6, wherein said step of densifying a layer of hydroxylapatite is accomplished using rapid thermal annealing.

8. The method as described in claim 6, wherein said step of densifying a layer of hydroxylapatite is accomplished using non-line-of-sight ion implantation.

* * * * *